(12) United States Patent
Sweitzer et al.

(10) Patent No.: US 11,331,202 B2
(45) Date of Patent: May 17, 2022

(54) MODULAR JAW AND ORTHOPEDIC IMPLANT EXTRACTION TOOL

(71) Applicant: Shukla Medical, St. Petersburg, FL (US)

(72) Inventors: Zachary Robert Sweitzer, Keyport, NJ (US); Nicholas Christopher Keach, Lutz, FL (US)

(73) Assignee: Shukla Medical, St. Petersburg, FL (US)

( * ) Notice: Subject to any disclaimer, the term of this patent is extended or adjusted under 35 U.S.C. 154(b) by 177 days.

(21) Appl. No.: 16/658,606

(22) Filed: Oct. 21, 2019

(65) Prior Publication Data

US 2021/0059836 A1 Mar. 4, 2021

Related U.S. Application Data

(63) Continuation-in-part of application No. 29/703,792, filed on Aug. 29, 2019, now Pat. No. Des. 937,415.

(51) Int. Cl.
*A61F 2/46* (2006.01)
*A61F 2/30* (2006.01)

(52) U.S. Cl.
CPC .. *A61F 2/4603* (2013.01); *A61F 2002/30479* (2013.01); *A61F 2002/4619* (2013.01); *A61F 2002/4622* (2013.01)

(58) Field of Classification Search
CPC ............ A61F 2/4603; A61F 2002/4619; A61F 2002/4622; B25B 7/04; B25B 7/22
See application file for complete search history.

(56) References Cited

U.S. PATENT DOCUMENTS

| 1,556,755 | A | * | 10/1925 | Burman | .................... B25B 7/02 |
| | | | | | 81/423 |
| 4,576,067 | A | * | 3/1986 | Buck | ..................... E21B 19/161 |
| | | | | | 269/283 |
| 10,085,852 | B2 | | 10/2018 | Sweitzer | |
| 2007/0100347 | A1 | | 5/2007 | Stad et al. | |
| 2011/0296963 | A1 | | 12/2011 | Steele et al. | |
| 2012/0318107 | A1 | * | 12/2012 | Mann | ........................ B25B 7/14 |
| | | | | | 81/319 |
| 2013/0166032 | A1 | | 6/2013 | McDonough et al. | |
| 2016/0270929 | A1 | * | 9/2016 | Sweitzer | ................. A61F 2/461 |

OTHER PUBLICATIONS

Extended European Search Report for European Patent Application No. 20203140.7 dated Mar. 25, 2021.

* cited by examiner

*Primary Examiner* — Kevin T Truong
*Assistant Examiner* — Tracy L Kamikawa
(74) *Attorney, Agent, or Firm* — Kim IP Law Group LLC

(57) ABSTRACT

A modular jaw for attachment to an orthopedic implant extraction tool that includes an elongated body, a claw about a distal end of the elongated body for engaging an object, and a locking mechanism about a posterior end of the elongated body for engaging the orthopedic implant extraction tool. The locking mechanism includes a dovetail lock, a detent mounted to the dovetail lock, and a distally facing surface about a proximal end of the elongated body.

20 Claims, 11 Drawing Sheets

MODULAR JAW AND ORTHOPEDIC IMPLANT EXTRACTION TOOL

BACKGROUND OF THE DISCLOSURE

Exemplary embodiments of the subject disclosure relate generally to the field of medical device implant extraction tools. Specifically, the subject disclosure relates to an orthopedic implant extraction tool having a modular jaw.

Orthopedic implant extraction tools contain jaws to grasp an orthopedic implant. Frequently, these jaws can break upon continued use, often as a result of improper or unintended use of the tool. Accordingly, there remains a need for a modular jaw that can withstand the clamping and extraction forces placed upon the orthopedic implant extraction tool, but that can be used as a consumable part and replaced, as needed, without requiring replacement of the entire tool.

SUMMARY OF THE DISCLOSURE

One aspect of the subject disclosure provides a modular jaw for attachment to an orthopedic implant extraction tool. The modular jaw includes an elongated body, a claw about a distal end of the elongated body for engaging an object, a locking mechanism about a posterior end of the elongated body for engaging the orthopedic implant extraction tool, and a distally facing surface about a proximal end of the elongated body. The locking mechanism includes a dovetail lock and a detent mounted to the dovetail lock.

In one embodiment, the locking mechanism extends from about a midportion of the elongated body. The dovetail lock can be a tapered dovetail lock and the detent can be a ball detent. In one embodiment, the modular jaw includes a posteriorly extending tapered tenon (e.g., a curved posteriorly extending tapered tenon) about the proximal end of the elongated body. The elongated body can include a first planar posterior end and a second planar posterior end offset from the first planar posterior end, and the claw can be in the form of a posteriorly extending tapered lip.

Another embodiment of the subject disclosure provides an orthopedic implant extraction tool that includes a handle, a gripping handle pivotably connected to the handle, and the instantly described modular jaw connectable to the handle. The orthopedic implant extraction tool further includes a movable jaw connected to the gripping handle, and a shaft connectable to the handle for locking the modular jaw in position.

In one embodiment, the handle includes a cooperating locking mechanism engageable with the locking mechanism of the modular jaw, such as a corresponding dovetail lock about an anterior face of the handle for engaging the dovetail lock of the modular jaw. The shaft has an overall diameter that overlaps with, and engages, a proximal end of the modular jaw when connected to the handle.

Another aspect of the subject disclosure provides an orthopedic implant extraction tool that includes a handle, a gripping handle pivotably connected to the handle, and a modular stationary jaw connectable to the handle. The modular stationary jaw includes a body, a claw about a distal end of the body, and a locking mechanism for engaging the gripping handle. The locking mechanism includes a dovetail lock, a detent, and a distally facing surface about a posterior end of the body. The orthopedic implant extraction tool further includes a movable jaw connected to the gripping handle, and a shaft connectable to the handle for locking the modular stationary jaw in position.

In one embodiment, the handle includes a cooperating locking mechanism engageable with the locking mechanism of the modular stationary jaw. The handle can include a corresponding dovetail lock about an anterior face of the handle for engaging the dovetail lock of the modular stationary jaw. The handle can further include a fastener about a posteriorly facing end of the handle.

In one embodiment, the shaft has an overall diameter that overlaps with a proximal end of the modular stationary jaw when connected to the handle. In certain embodiments, the shaft directly engages the modular stationary jaw when connected to the handle.

BRIEF DESCRIPTION OF THE SEVERAL VIEWS OF THE DRAWINGS

The following detailed description of an exemplary embodiment of the subject disclosure will be better understood when read in conjunction with the appended drawings. For the purpose of illustrating the present disclosure, there is shown in the drawings an exemplary embodiment. It should be understood, however, that the subject application is not limited to the precise arrangements and instrumentalities shown.

DETAILED DESCRIPTION

Reference will now be made in detail to an exemplary embodiment of the subject disclosure illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as upper, lower, top, bottom, above, below and diagonal, are used with respect to the accompanying drawings. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Figure 8:
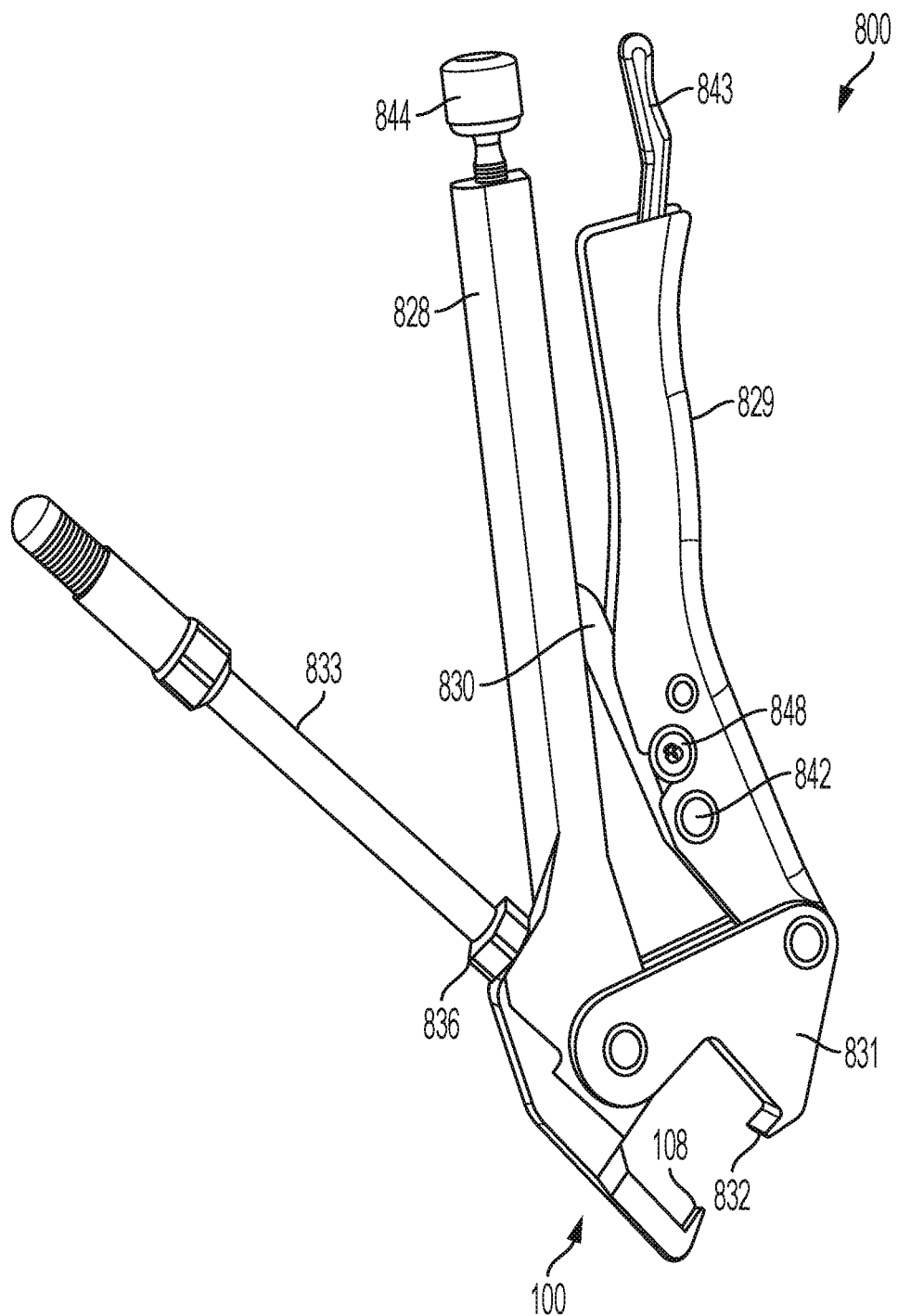
FIG. 8 is a perspective view of an orthopedic implant extraction tool that includes the modular jaw of FIG. 1.

Referring now to the drawings, FIG. 1-7 illustrate a modular jaw 100 for attachment to an orthopedic implant extraction tool, such as, for example, the orthopedic implant extraction tool 800 shown in FIG. 8. The modular jaw 100 includes an elongated body 101, a claw 102 about a distal end 103 of the elongated body, and a locking mechanism 104 about a posterior end 105 of the elongated body for engaging the orthopedic implant extraction tool. The modular jaw further includes a distally facing surface 106 about a proximal end 107 of the elongated body.

Figure 1:
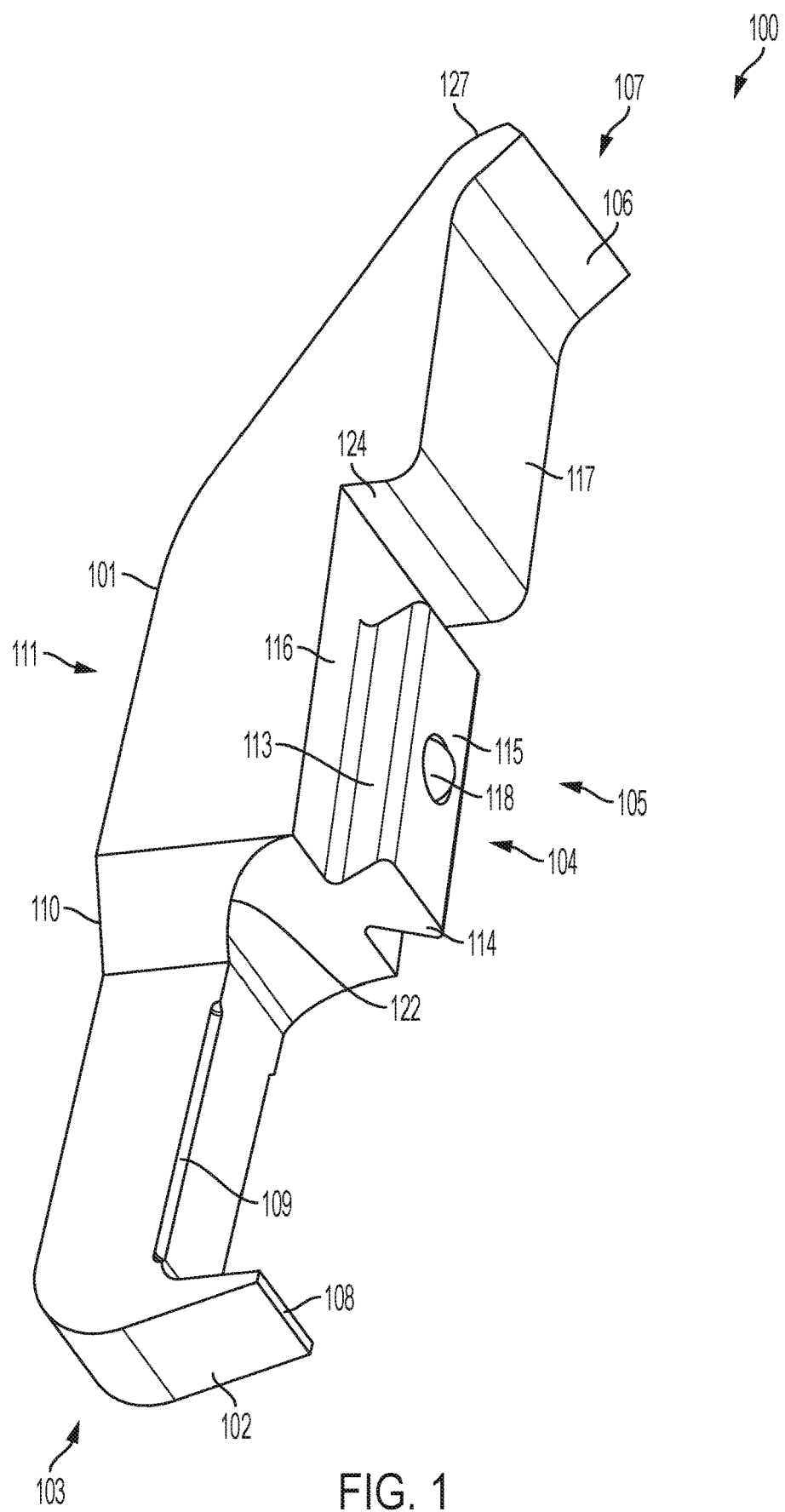
FIG. 1 is a perspective view of a modular jaw in accordance with an exemplary embodiment of the subject disclosure.

The distal end 103 includes the claw 102 that is configured, e.g., as a lip for engaging an object such as an orthopedic implant, such as a tibial orthopedic implant (tibial tray) used in knee replacement surgery. The lip 108 can, in certain exemplary embodiments, be in the form of a sharp edge to penetrate the interface of the orthopedic implant and bone, which can include implant-bone cement or an implant-bone boundary. As shown in FIG. 1, the lip 108 is a posteriorly extending tapered lip that is slightly tapered inward from the furthest distal reach of the distal end 103.

Figure 4:
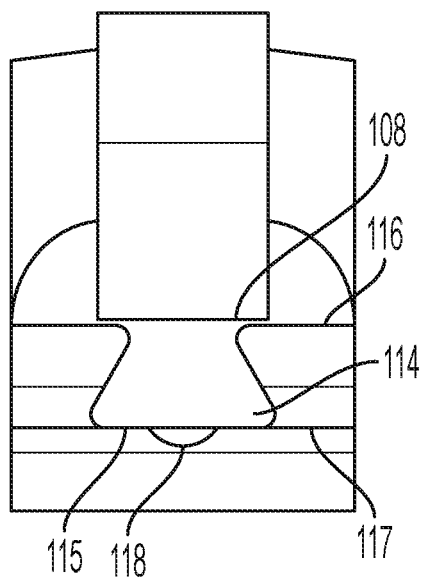
FIG. 4 is a bottom plan view of the modular jaw of FIG. 1.
Figure 5:
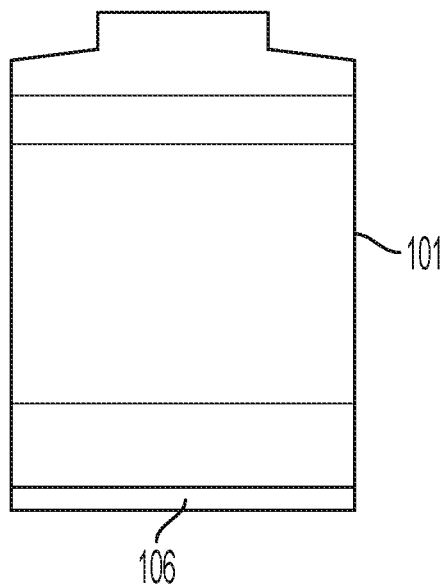
FIG. 5 is a top plan view of the modular jaw of FIG. 1.

As best shown in FIG. 4, the lip 108 defines a posterior end of the claw 102 that terminates about a first planar posterior end 116. Alternatively, in other exemplary embodiments, a longer lip can be provided that extends to or before a second planar posterior end 117 that is offset from the first planar posterior end 116.

Figure 2:
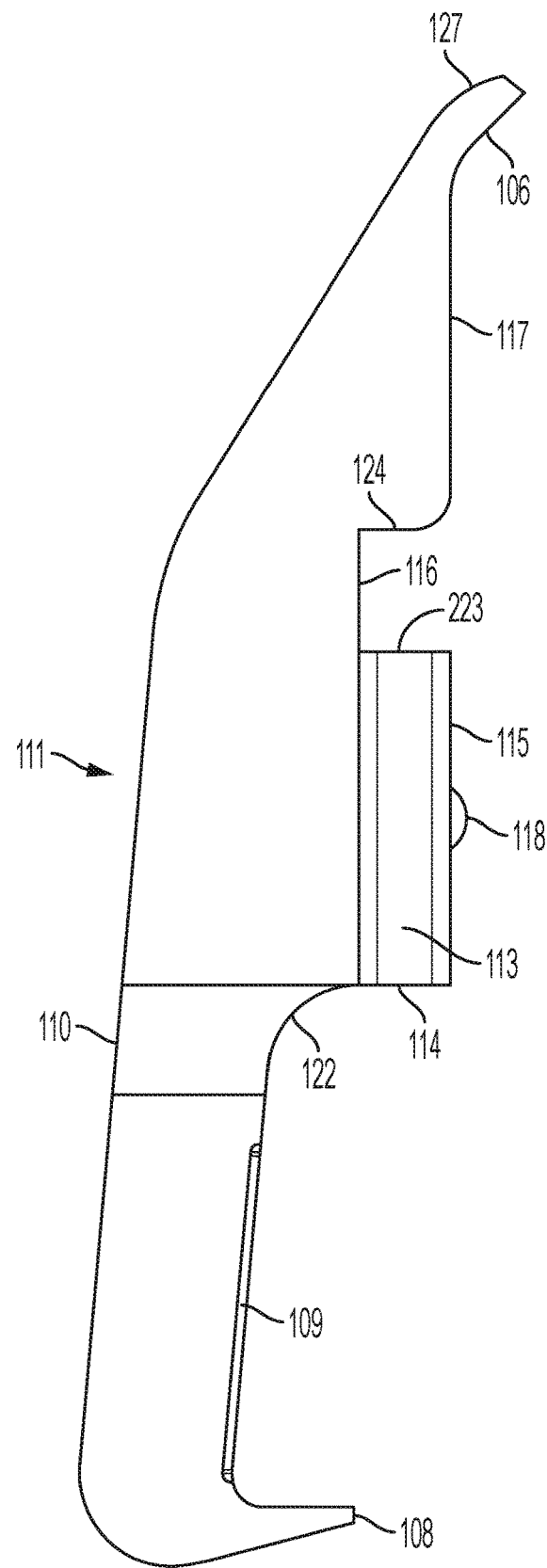
FIG. 2 is a left side view of the modular jaw of FIG. 1.
Figure 6:
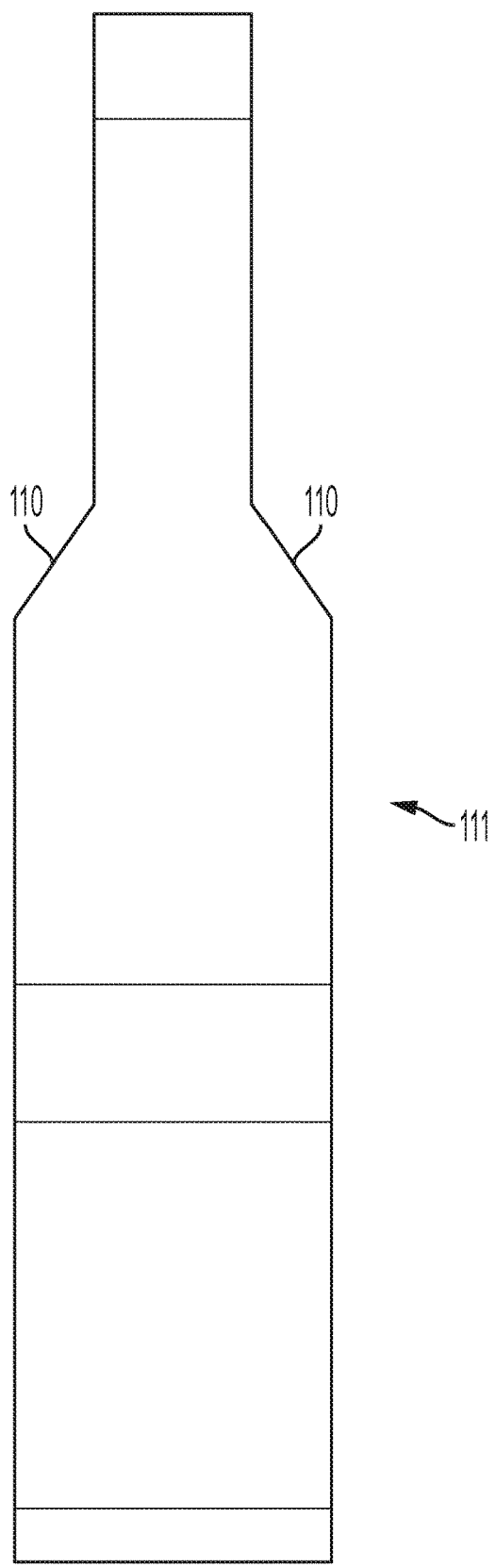
FIG. 6 is a front view of the modular jaw of FIG. 1.
Figure 7:
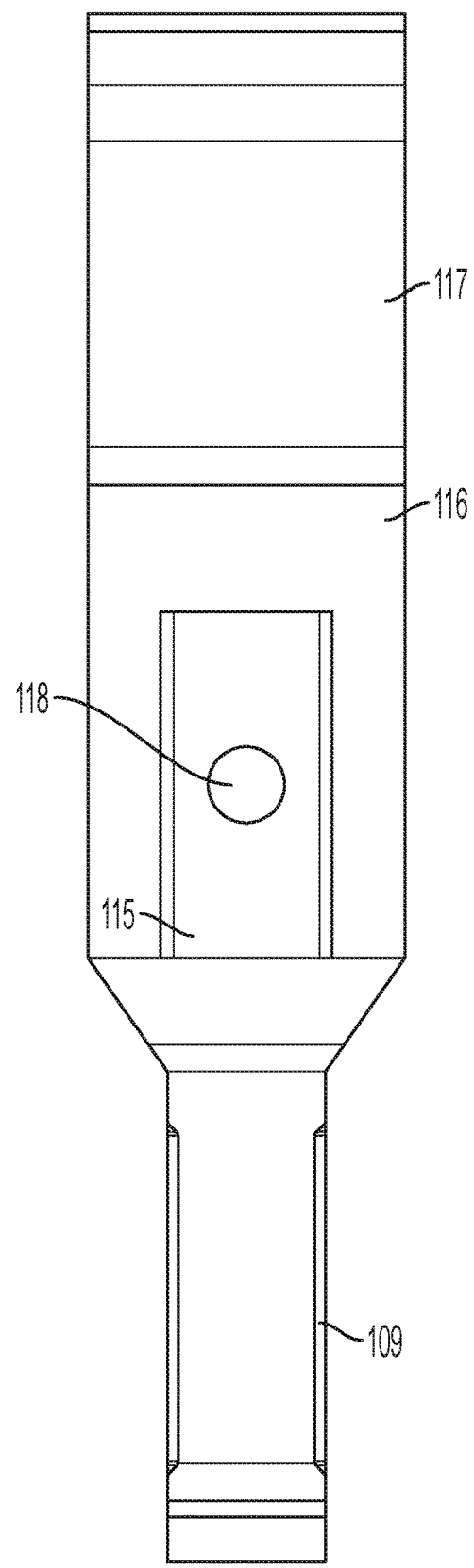
FIG. 7 is a rear view of the modular jaw of FIG. 1.

The elongated body 101 proceeds from the distal end 103 with a width that is the same, or substantially similar to, the width of the lip 108. The edges along the posterior end 105 of this section are provided in this exemplary embodiment with relived edges 109. The elongated body 101 then flares outwardly at flares 110 toward the proximal end to provide a second, larger width at along a midportion 111 of the elongated body, this second, larger width continuing for the remainder of the elongated body, as best shown in FIG. 6. Posterior flares 122 similarly extend outward to provide the second, larger width, but also extend posteriorly to provide an increased width, as best shown in FIG. 2. The posterior flares 122 terminates about the plane defined by the first planar posterior end 116. For example, the second, larger width can be 1.5, 2, 2.5 or 3 times the width of the lip 108, though other dimensioning could be provided.

About the posterior end 105 of the elongated body, a locking mechanism 104 is provided. The locking mechanism extends from the midportion 111 of the elongated body 101. In this particular embodiment, the locking mechanism includes a dovetail lock 113, which tapers to provide an increasing width as one proceeds posteriorly (from left to right as oriented in FIG. 1), reaching a maximum at a posterior dovetail lock plane 115. The dovetail lock 113 is provided with a pair of faces, distal face 114 and proximal face 223 that are generally trapezoidal shaped.

The dovetail lock 113 includes the posterior dovetail lock plane 115 that is generally parallel to the first planar posterior end 116 from which the dovetail lock 113 originates. As best shown in FIG. 4, the dovetail lock plane 115 is along the same plane as second planar posterior end 117 and has a width substantially equal to the width of the lip 108. As will be discussed in connection with FIG. 10 below, the locking mechanism 104 is shaped to engage with a corresponding locking mechanism 1021 that can be located on an anterior face 1041 of a handle to the orthopedic implant extraction tool.

Figure 10:
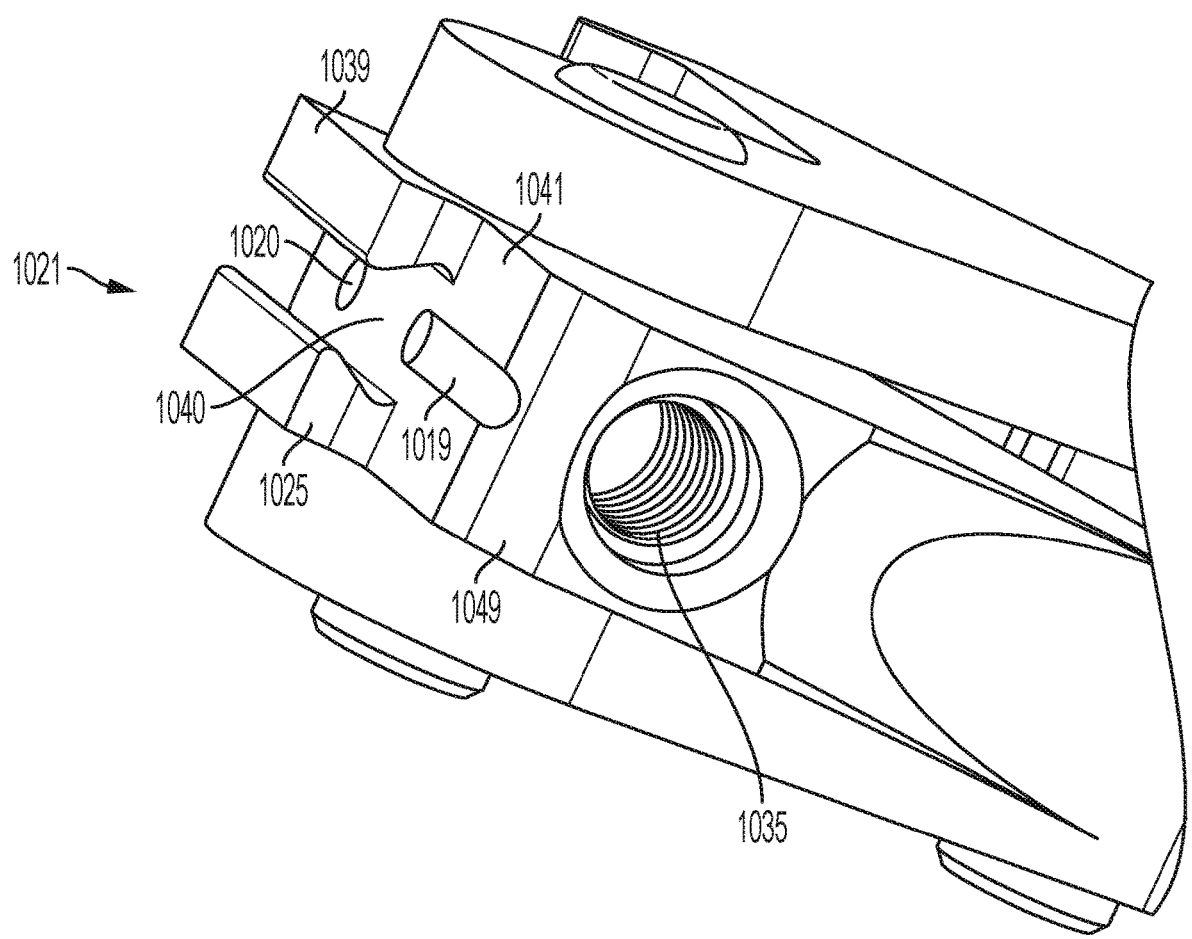
FIG. 10 is an enlarged partial perspective view of the orthopedic implant extraction tool of FIG. 8, shown with certain components omitted for purposes of clarity.

Detent 118 is mounted on the posterior dovetail lock plane 115 of the dovetail lock 113. In this particular embodiment, the detent 118 is a ball detent that is provided with a ball biased outwardly by a compression spring (not shown). The detent 118 is mounted about a central portion of the dovetail lock, where it can engage components of the corresponding locking mechanism 1021, particularly, a ball detent track 1019 and a ball detent seat 1020 located on the anterior face 1041 of the handle 828, as best shown in FIG. 10 and discussed below. Detent 118 serves to hold the modular jaw 100 in place during assembly, as discussed below.

The dovetail lock 113 terminates to form the proximal face 223 of the dovetail lock. A posteriorly extending stop 124 is located axially with respect to the distal face 114 and the proximal face 223 of the dovetail lock. In this embodiment, the stop 124 forms a face that is dimensioned to engage a complementarily shaped surface of the orthopedic implant extraction tool, such as, for example, stop surfaces 1025 shown in FIG. 10. The stop 124, when engaged with the stop surface 1025, prevents further movement of the modular jaw 100 in the distal direction when the modular jaw is assembled onto the orthopedic implant extraction tool, and also positions the detent 118 over the detent seat 1020 of the orthopedic implant extraction tool.

Figure 3:
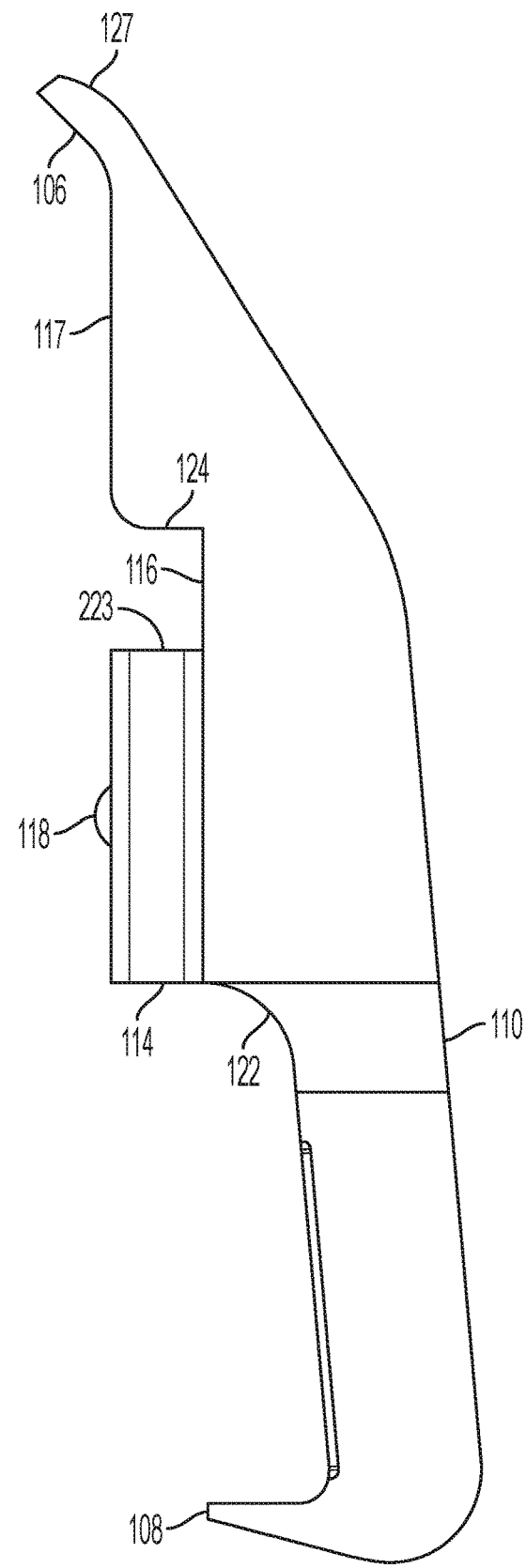
FIG. 3 is a right side view of the modular jaw of FIG. 1.

In this particular embodiment, the posteriorly extending stop 124 provides the offset between the first planar posterior end 116 and the second planar posterior end 117. As best shown in FIGS. 2-3, the first planar posterior end 116 is parallel to, or substantially parallel to, the second planar posterior end 117, with the stop 124 oriented perpendicular to both the first planar posterior end and the second planar posterior end.

The proximal end 107 of the elongated body 101 tapers along the portion of the jaw defined by the second planar posterior end 117. The second planar posterior end 117 meets the distally facing surface 106 that is also provided about the elongated body 101. The proximal end 107 continues to taper along the portion defined by the distally facing surface 106 to define a posteriorly extending tapered tenon 127 about the proximal end 107 of the elongated body (and about the posterior end 105). The distally facing surface 106 is provided at an end of the posteriorly extending tapered tenon 127, as best shown in FIG. 1. This distally facing surface 106 is provided about the proximal end 107 and the posterior end 105 of the elongated body 101.

The modular jaw 100 is attachable to the orthopedic implant extraction tool 800 shown in FIGS. 8-11. Tool 800 includes a handle 828 that is connectable to the modular jaw 100, and a gripping handle 829 coupled to the handle 828 via a locking link 830. The gripping handle 829 is pivotably connected to the handle 828 via movable jaw 831, which in turn is provided with a second claw, e.g., in the form of a lip 832 that, like lip 108 of the modular jaw 100, is sized and shaped to grasp an orthopedic implant such as, for example, a tibial implant tray used in knee replacement surgery.

A shaft 833 is connected to the handle 828 via fastener 934 located about a posteriorly facing end 937 of the handle. Though not limited thereto, the shaft 833 can be, for example, a shaft to an extractor extension, such as a connecting rod or an extraction rod.

In this particular embodiment, the fastener 934 is a threaded bore. The shaft 833 can include a threading 1251 about a distal end of the shaft with threads shaped to engage with the threads 1035 of the threaded bore. The shaft 833 can further include a head 836, or the head 836 can be provided by a nut included as part of the shaft 833. In either scenario, the head 836 and/or shaft 833 defines an overall diameter of the shaft in the particular embodiment disclosed in FIG. 8. The head 836 is optional, and not present in certain embodiments, in which case the shaft defines the overall diameter.

Figure 12:
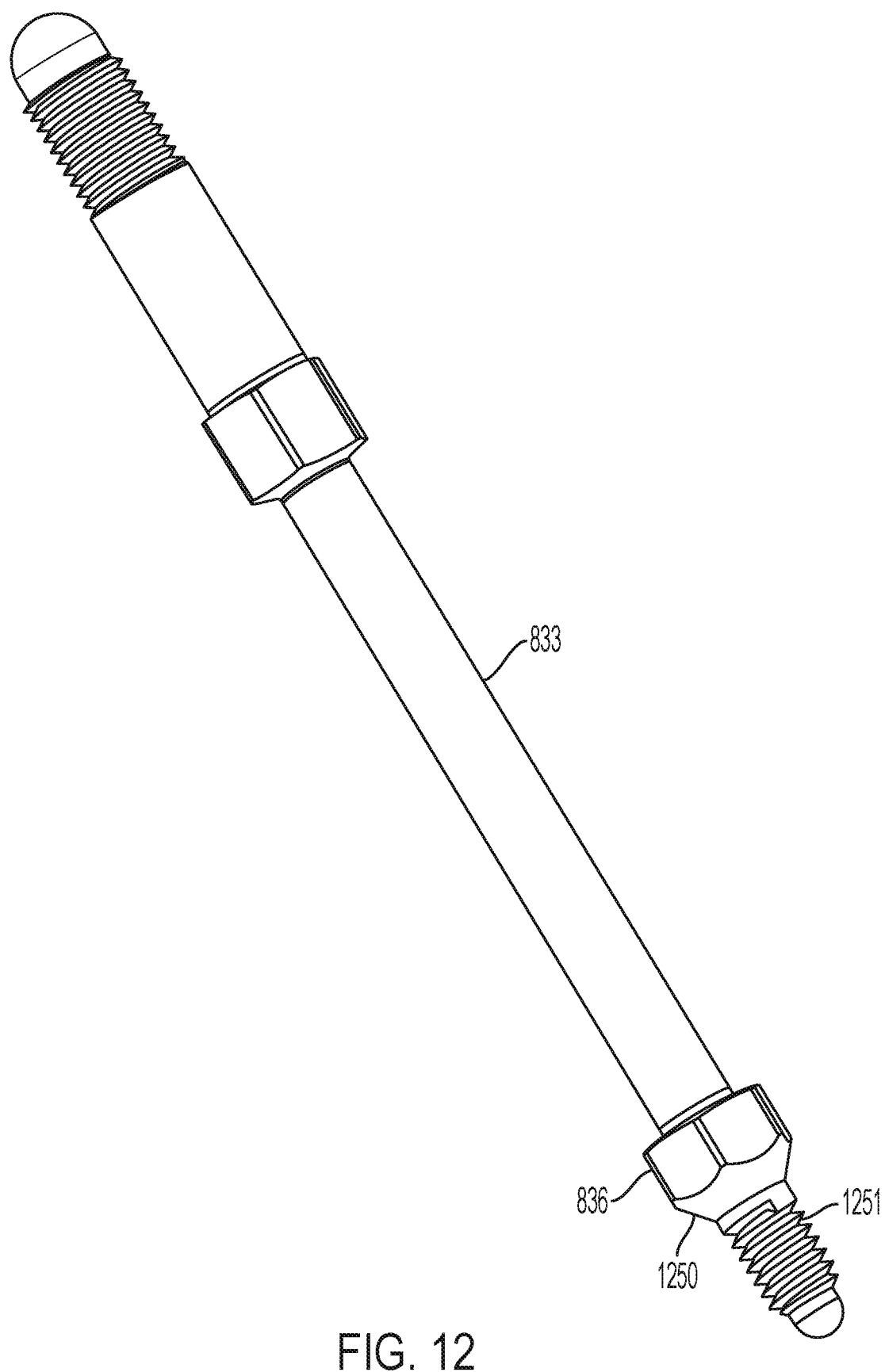
FIG. 12 is a perspective view of a shaft of the orthopedic implant extraction tool of FIG. 8.

The shaft 833 can be provided with a larger diameter as it exits handle 828, as compared to the diameter of the shaft at the threading 1251 that internally engages the fastener 934 (e.g., a threaded bore). As shown best in FIG. 12, the shaft 833 can include, for example, a flare 1250 that provides a progressively larger diameter proceeding from the threading 1251 to the head 836 of the shaft. Alternatively, for example, a beveled nut could be employed to provide the overall diameter of the shaft 833. Other configurations can be employed so that the shaft provides an overall diameter that overlaps with a proximal end of the modular stationary jaw when connected to the handle 828.

Figure 11:
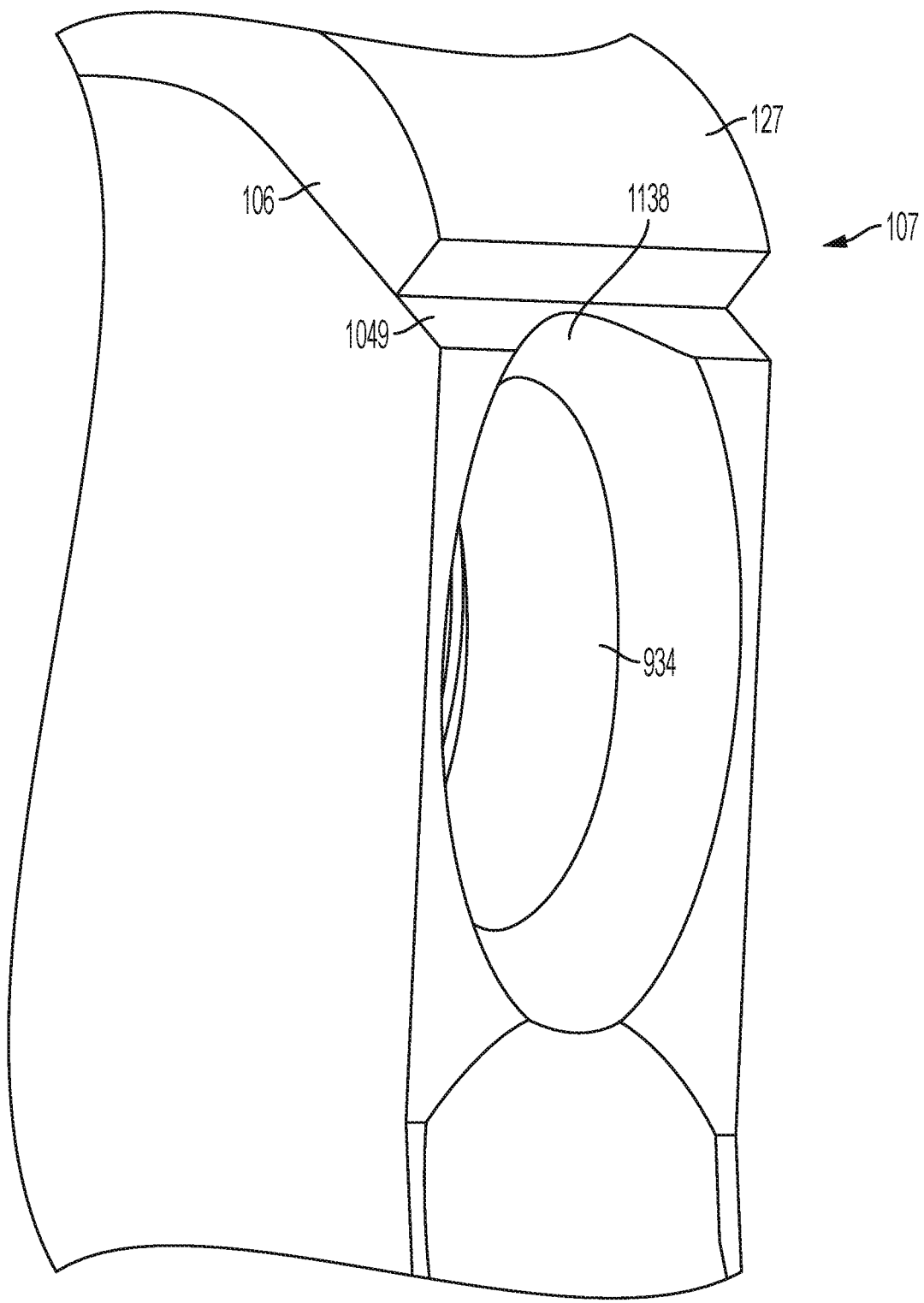
FIG. 11 is another enlarged partial perspective view of the orthopedic implant extraction tool of FIG. 8, shown with certain components omitted for purposes of clarity.

As shown best in FIG. 11, the fastener 934 is provided with beveled edges 1138 to accommodate and seat the larger diameter of the shaft (e.g. at the flare 1250). When the shaft 833 is connected to the handle 828 via the fastener 934, a part of the shaft directly contacts the proximal end of the modular jaw 100.

With reference to FIG. 10, the handle 828 includes a corresponding locking mechanism 1021 which corresponds to the locking mechanism 104. In this particular embodiment, the locking mechanism 124 is a male locking mechanism and the corresponding locking mechanism 1021 is a female locking system. The corresponding locking mechanism 1021 of the handle 828 includes, in this particular embodiment, a corresponding dovetail lock 1039 provided about the anterior face 1041 of the handle. The corresponding dovetail lock 1039 contains a passageway 1040 shaped to receive the distal face 114 of the dovetail lock 113. The width of the passageway 1040 decreases as one proceeds anteriorly (from bottom to top as oriented in FIG. 10) to correspond to the increasing width of the dovetail lock 113. This dovetail engagement provides a secure engagement of the modular jaw 100 in response to a clamping force.

The anterior face 1041 further includes a ball detent track 1019 and a ball detent seat 1020. The ball detent track 1019 is axially aligned with the ball detent seat 1020, both of which being axially aligned with stop 124, and are each sized to receive the ball to the detent 118. The ball detent track 1019 serves to allow the modular jaw to be easily slid into the handle 828. A sloped face 1049 is provided proximal to the anterior face 1041 and provides a proximally faced surface, as shown in FIG. 10. Sloped face 1049 is shaped complementary to the distally facing surface 106 to directly engage the distally facing surface 106 when the modular jaw is secured onto the handle.

Orthopedic implant extraction tool 800 can include other standard components, such as those components disclosed in the orthopedic implant extraction tools disclosed in U.S. Pat. No. 10,085,852 which is hereby incorporated by reference in its entirety.

Figure 9:
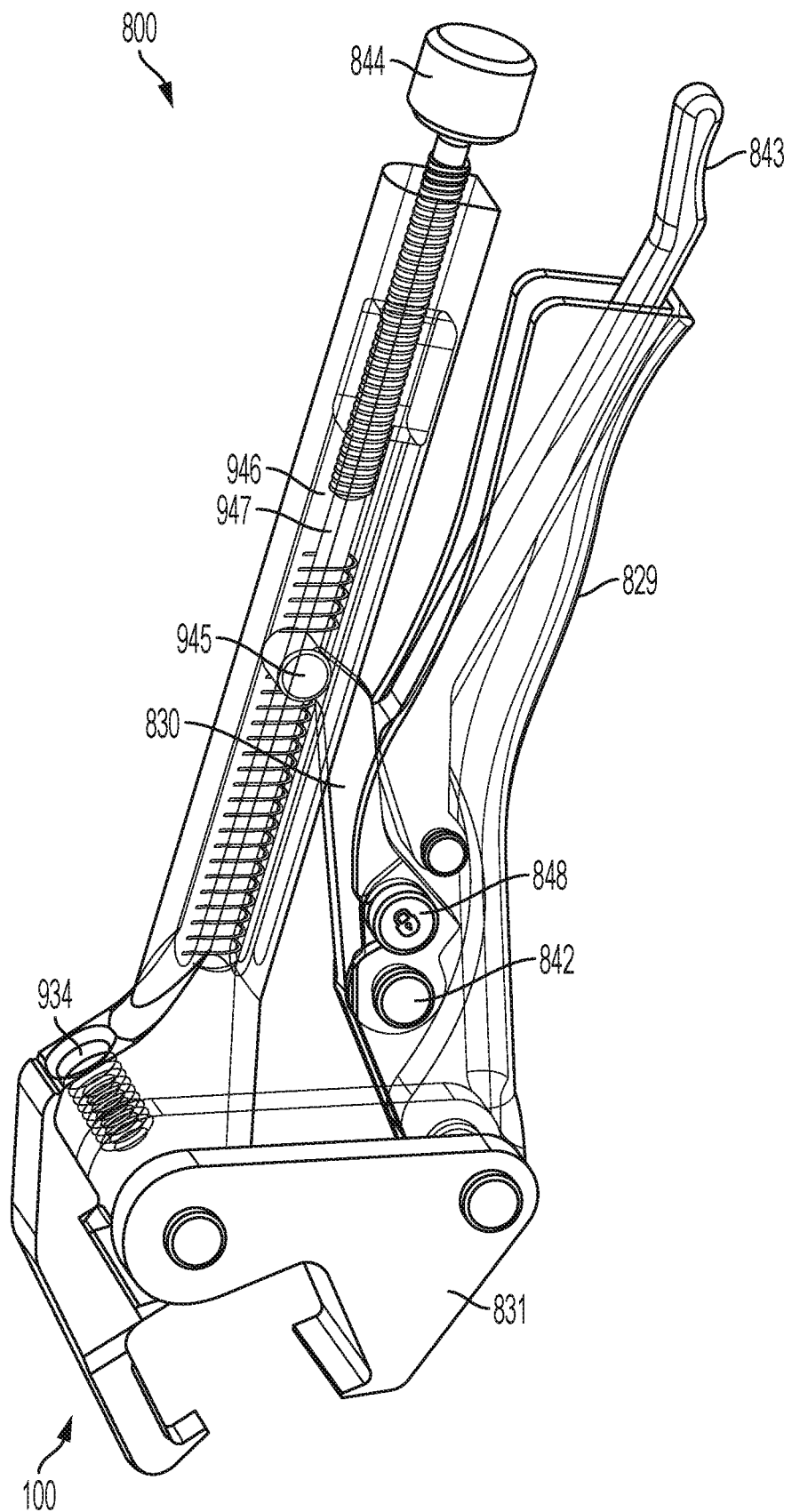
FIG. 9 is another perspective view of the orthopedic implant extraction tool of FIG. 8, shown with certain components omitted or rendered transparent for purposes of clarity.

For example, as best shown in FIG. 9, in which the handle 828 and the gripping handle 829 is rendered transparent solely for purposes of illustration, the locking link 830 has one end mounted for rotation about pin 842 in the gripping handle 829 with the other end 945 mounted within a longitudinal groove 946 that is located within the handle 829. A lock 843, secured within the gripping handle 829, can be manually manipulated such that it contacts the locking link 830 to prevent the lips 108 and 832 from closing past the adjusted opening provided by a thumb screw 844. Thumb screw 844 is connected to a shaft 947 that engages end 945 of the locking link 830 and serves to adjustably limit the range of movement of the locking link 830, which in turn serves to limit the extent to which the lips 108 and 832 can be closed. A locking pin 848 is provided that is connected to a sliding rod (not shown) such that, when the locking pin 848 is depressed, moves the sliding rod to engage the locking link 830 to prevent movement of the locking link and lock the handles in their current position. These components of the tool 800 are provided for purposes of illustration only. The modular jaw 100 can be used with other tools having different designs and is not limited to use with the orthopedic implant extraction tool 800 described herein.

In operation, the distal face 114 of the dovetail lock 113 of the modular jaw 100 is slid into the passageway 1040 of the corresponding dovetail lock 1039. This engagement is aided placing the ball from detent 118 into the ball detent track 1019. When the stop 124 of the modular jaw engages the stop surface 1025, the ball to the detent is seated in ball detent seat 1020 and the modular jaw 100 is fully engaged with the handle 828. As noted, a compression spring (not shown) biases the ball against ball detent seat 1020.

When the modular jaw 100 is fully engaged with the handle 828, shaft 833 is engaged with fastener 934 by screwing the shaft 833 into the fastener 934 via threading 1251. In this particular embodiment, the fastener 934 is a threaded bore. Doing so causes the shaft 833 to directly contact and engage the proximal end 107 of the modular jaw, which in turn renders the tool 800 ready for use. More particularly, direct contact of the shaft with the proximal end 107 of the modular jaw secures distally facing surface 106 against the sloped face 1049 of the handle to lock the modular jaw into place so that the modular jaw is secure under all ranges of motion. To remove the modular jaw 100, the shaft 833 is removed from the handle 828, and then the modular jaw can be slid out from the handle in the opposite direction from which it was engaged.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the claims defined herein.

The invention claimed is:

1. A modular jaw for attachment to an orthopedic implant extraction tool, the modular jaw comprising:
   an elongated body;
   a posteriorly extending claw defining a distal end of the elongated body for engaging an object;
   a locking mechanism extending posteriorly from a posterior end surface of the elongated body for engaging the orthopedic implant extraction tool, the locking mechanism including:
      a dovetail lock, and
      a detent mounted to the dovetail lock; and
   a distally facing surface extending posterior to the locking mechanism about a proximal end of the elongated body.

2. The modular jaw of claim 1, wherein the locking mechanism extends from about a longitudinal midportion of the elongated body.

3. The modular jaw of claim 1, wherein the dovetail lock is a tapered dovetail lock.

4. The modular jaw of claim 1, wherein the detent is a ball detent.

5. The modular jaw of claim 1, further comprising a posteriorly extending tapered tenon about the proximal end of the elongated body.

6. The modular jaw of claim 5, wherein the posteriorly extending tapered tenon is curved.

7. The modular jaw of claim 1, wherein the posterior end surface is a first planar posterior end surface and the elongated body further includes a second planar posterior end surface offset from the first planar posterior end surface.

8. The modular jaw of claim 7, wherein the claw includes a posterior end that terminates about a plane defined by one of the first or second planar posterior end surfaces.

9. The modular jaw of claim 1, wherein the claw is a posteriorly extending tapered lip.

10. An orthopedic implant extraction tool comprising:
    a handle;
    a gripping handle pivotably connected to the handle;
    the modular jaw of claim 1, connectable to the handle;
    a movable jaw connected to the gripping handle; and
    a shaft connectable to the handle for locking the modular jaw in position.

11. The orthopedic implant extraction tool of claim 10, wherein the handle includes a second locking mechanism engageable with, and shaped complementary to, the locking mechanism of the modular jaw.

12. The orthopedic implant extraction tool of claim 10, wherein the handle includes a corresponding dovetail lock about an anterior face of the handle for engaging the dovetail lock of the modular jaw.

13. The orthopedic implant extraction tool of claim 10, wherein the shaft has an overall diameter that overlaps with a proximal end of the modular jaw when connected to the handle.

14. The orthopedic implant extraction tool of claim 10, wherein the shaft directly engages the modular jaw when connected to the handle.

15. An orthopedic implant extraction tool comprising:
    a handle;
    a gripping handle pivotably connected to the handle;
    a modular stationary jaw connectable to the handle, the modular stationary jaw including:
       a body,
       a posteriorly extending claw about a distal end of the body;
       a locking mechanism extending posteriorly from a posterior end surface of the body for engaging the handle, the locking mechanism including:
          a dovetail lock, and
          a detent, and
       a distally facing surface extending posterior to the locking mechanism about a proximal end of the body;
    a movable jaw connected to the gripping handle; and
    a shaft connectable to the handle for locking the modular stationary jaw in position.

16. The orthopedic implant extraction tool of claim 15, wherein the handle includes a second locking mechanism engageable with, and shaped complementary to, the locking mechanism of the modular stationary jaw.

17. The orthopedic implant extraction tool of claim 15, wherein the handle includes a corresponding dovetail lock about an anterior face of the handle for engaging the dovetail lock of the modular stationary jaw.

18. The orthopedic implant extraction tool of claim 15, wherein the handle includes a fastener about a posteriorly facing end of the handle.

19. The orthopedic implant extraction tool of claim 15, wherein the shaft has an overall diameter that overlaps with a proximal end of the modular stationary jaw when connected to the handle.

20. The orthopedic implant extraction tool of claim 15, wherein the shaft directly engages the modular stationary jaw when connected to the handle.

* * * * *